United States Patent [19]

Burrows

[11] 3,962,467
[45] June 8, 1976

[54] PROCESSES OF DRYING YEAST

[75] Inventor: Sidney Burrows, Tillicoultry, Scotland

[73] Assignee: The Distillers Company (Yeast) Limited, Morden, England

[22] Filed: July 22, 1974

[21] Appl. No.: 490,442

[30] Foreign Application Priority Data

July 23, 1973 United Kingdom............... 34895/73

[52] U.S. Cl................................. 426/62; 426/465; 195/74; 195/98
[51] Int. Cl.²......................................... C12C 11/30
[58] Field of Search ................. 426/60, 61, 62, 226, 426/465, 473; 195/74, 98

[56] References Cited

UNITED STATES PATENTS

| | | | |
|---|---|---|---|
| 3,041,249 | 6/1962 | Chen et al. | 195/74 |
| 3,615,685 | 10/1971 | Trevelyan | 195/98 X |
| 3,780,181 | 12/1973 | Trevelyan | 195/98 X |
| 3,843,800 | 10/1974 | Langejan | 426/60 X |

*Primary Examiner*—Raymond N. Jones
*Assistant Examiner*—R. A. Yoncoskie
*Attorney, Agent, or Firm*—Lawrence Rosen; E. Janet Berry

[57] ABSTRACT

A method is described for making active dried yeast in which the yeast is dried in a fluidized bed using warm air and in which the yeast temperature at the end of the process exceeds 50°C.

10 Claims, No Drawings

PROCESSES OF DRYING YEAST

Active dried yeast is well known and is made by drying particles of moist yeast until the dry matter content is, for example, from 90 to 97%. It is well known that the drying conditions, and in particular the temperature of the yeast during drying and the duration of the drying, significantly affect the final activity of the yeast. As a generality it has been accepted that high temperatures should be avoided during drying. A possible exception is when the yeast is dried by spray drying which necessarily involves higher temperatures, but then spray dried yeast tends to have rather poor activity.

Various drying methods other than spray drying are knwon. Commercially drum drying is probably the most widely used but fluidized bed drying has also been proposed in British Specifications Nos. 1,132,793 and 1,230,205. Again, all the indications are that high temperatures should be avoided. Thus in Specification No. 1,230,205 it is specifically stated that the yeast temperature must be 20° to 50°C preferably 30° to 35°C and in 1,132,793 the air temperature used for fluidising is generally 40°C, which means that the temperature of the yeast particles would be no higher than this.

As a result of these limitations a necessary consequence of all prior methods has been either that the drying takes rather a long time or that specially dehumidified air has to be used or that the drying has to be terminated at higher moisture contents (for example 8 to 10%) than might otherwise be preferred, for example 4 to 6%. These disadvantages have all previously been accepted as a necessary evil.

In the invention active dried yeast is made by drying particulate yeast in a fluidised bed that is fluidised using warm air, and in which the yeast temperature at least at the end of the drying is above 50°C.

It is very surprising that one can obtain satisfactory results despite all the previous contraindications that the yeast temperature must be below 50°C.

As a result of being able to use the higher temperature drying to low moisture contents, for example 4 to 6%, in reasonable drying times using air that has not been dehumidified is now possible.

The use of yeast temperatures above 50°C has to be adopted with some degree of caution and if the yeast is maintained at an undesirably high temperature for too long its activity can be seriously damaged. However in the invention it is possible easily to strike a satisfactory compromise between, on the one hand, the tendency to reduce the activity of the yeast and, on the other hand, the ability to dry more quickly and more easily to a lower moisture content, with resultant improved stability of the yeast.

In order that the advantages of the high temperature drying can be obtained the yeast must have the temperature of above 50°C for a significant period, e.g. at least 5 or 10 minutes. However the yeast must not have the temperature for too long and generally the yeast has it for less than half the total drying time or for less than 45 minutes, whichever is the lesser. Usually the temperature is above 50°C only for the last 30 minutes, and most preferably for the last 15 or 20 minutes, of the drying operation. Preferred times are thus between 10 and 45 minutes, most preferably 15 to 30 minutes. The temperature of the yeast is usually only above 50°C when the dry matter content in the yeast has exceeded 80%, and most preferably has exceeded 88%.

In practice all these parameters can be achieved without adjusting the drying conditions during the total drying process if the temperature of the air used for fluidising is not too high, for example if it is between 50° and 70°C or, more usually, between 50° and 60°C. With such air temperatures it is easy to select the rate of flow of air such that during the early stages of the drying, when the yeast has a very high moisture content, for example from 73 to 20%, the rate of evaporation is such that the temperature of the yeast is maintained below 50°C but that in the later stages of the drying, when the rate of evaporation is less, the temperature rises above 50°C.

Instead of relying upon a constant air temperature it is of course possible to adjust the air temperature during drying, the air temperature being, for example, 20° to 50°C and most preferably 30° to 40°C during the early drying stages and being, for example, 50° to 60°C in the later drying stages.

Whatever the air temperature and rate of flow used the conditions are generally so selected that the temperature of the yeast is always below 70°C and preferably below 60°C, and most preferably below 55°C.

The yeast that is subjected to drying in the invention normally has a dry matter content of from 27 to 40% by weight, most preferably 28 to 35%.

The yeast used in the drying method is preferably a strain of baker's yeast known to be suitable for the preparation of active dried yeast. The protein content of the yeast can be any convenient value but best activities are generally obtained when the nitrogen content is from 7 to 9%.

The particles that are subjected to fluidised bed drying preferably have a maximum dimension of 1.7 mm or less, and preferably have a dry matter content when introduced onto the bed of less than 50% by weight. Whilst it is possible to make particles that can be dried in the process of the invention merely by extrusion through an orifice having an appropriate small diameter, possibly followed by chopping the extruded strands, it is preferred to use methods that make particles smaller than is conveniently possible by these simple extrusion methods, so that the final product is a powder.

One preferred method comprises comminuting moist yeast, for example having a dry matter content of 27 to 40% by weight, under conditions of high shear, preferably in air. For example the yeast may be comminuted while exposed to air, and often while entrained in air, in a mill, for example containing blades that rotate at a speed greater than 2,000 r.p.m. Suitable comminution methods are described in British Patent Specification No. 1,140,016 and in Belgian Patent Specification No. 797062 (equivalent to British Patent Application No. 41144/72).

Another suitable method comprises spray drying a liquid yeast composition in air. For example a liquid yeast may be spray dried to provide particles having a moisture content of 40 to 50% dry matter. A suitable spray drying method is described in British Patent Specification No. 1,196,786. Greatly improved results are obtained when the yeast is only partly dried by spray drying, drying being completed by the process of the invention as described, compared to when the entire drying is by spray drying.

The total drying time will depend upon the rate of air flow, the temperature used and the loading on the screen. The rate of air flow may be for example from 5 to 15 lbs/lb wet yeast/min. The humidity of the air used may be at ambient humidity. The yeast loading on the screen may be for example 0.005 to 0.05 lbs preferably about 0.02 lbs, per square centimetre. By appropriate choice of conditions the drying time can be from, for example, 10 to 150 minutes, most preferably 30 to 120 minutes.

The dried yeast obtained in the process preferably has a dry matter content of at least 92% and most preferably 94 to 97%.

The properties of the yeast after drying at the high temperatures used in the invention may be improved by including various additives in the yeast prior to the drying process. Suitable additives include wetting agents. Amounts are usually, for example, from 0.1 to 5% and most preferably from 0.5 to 3% based on the dry weight of the yeast.

The wetting agent is preferably an ester, preferably a long chain aliphatic ester of an aliphatic hydroxy compound.

Suitable wetting agents include an ester of (1) a polyglycerol with a saturated fatty acid or (2) sorbitan with a saturated $C_{16}$ to $C_{18}$ fatty acid.

1. may be formed by esterifying a mixture of polyglycerols with a $C_{16}$ to $C_{18}$ fatty acid, for example with palmitic acid or stearic acid or with mixtures consisting predominantly of either or both of these. The resultant product is mainly a monoester although it does contain some di or higher esters and it also contains some, e.g. up to 10%, unesterified fatty acid. A suitable material is sold under the trade name "ADMUL Polyester 57" and the preparation of this is described in pages 27 and 28 of Process Biochemistry, December 1972.

2. is generally an ester both of sorbitans (these being 1,4-anhydroglucitol and 3,6-anhydroglucitol) and isosorbide this being 1,4- and 3,6-dianhydroglucitol. The fatty acid used for forming the ester is generally palmitic or stearic acid or mixtures consisting predominantly of either or both of these. The product is mainly a mixed monoester and diester and generally also contains some, e.g. up to 2%, free fatty acid. The production of suitable esters is described in U.S. Patent Specification No. 2,322,821. Suitable materials are available under the trade names "SPAN" 40 and "SPAN" 60. "SPAN" 40 contains about 35% or less of each of the mono- and dipalmitate and up to 2% of the free acid, with the balance unreacted sugar alcohol and anhydride. "SPAN" 60 contains about 45% or less of each of the mono- and distearate and up to 2% of the free acid, with the balance unreacted sugar alcohols and anhydride. Other products that may be used are the corresponding esters of hexitans and hexides, for example obtained by esterification of mannitol or other hexitol.

Other additives that may be used include polyols such as glycerol, sorbitol and inositol and carbohydrates or other swelling agents, for example carboxymethyl cellulose.

The following are examples of the invention.

EXAMPLE 1

A cake of moist compressed yeast was formed having a dry matter content of 33%. The yeast had a nitrogen content of 7.4% and a phosphate ($P_2O_5$) content of 2.6%, both these percentages being based on dry matter content. It was comminuted into particles having a diameter of 0.1 to 1 mm. In this example comminution was effected in a mill in which blades relate at high speed, e.g. as described in Belgian Patent Specification No. 797062, but other methods of obtaining this or similar particle size, e.g. other comminution methods or spray drying, could be used.

The comminuted yeast was loaded into a chamber 76 cm in diameter and the base of which was formed by a screen having apertures 200 mesh. The total load was 90 lbs wet yeast, this being a screen loading of 0.02 lb per square centimetre.

The particulate yeast was fluidised by passing up through the screen air having a temperature of 52°C and which had been obtained by heating atmospheric air which had a pressure of 770 mm, a temperature of 18°C and a humidity of 62%. This air at 52°C was passed through the screen for 110 minutes and in the later stages of the operation the yeast particles themselves had the same temperature as the air, 52°C. At the end of the drying process the yeast had a dry matter content of 95.9%.

The active dried yeast, when tested in the Fermentometer test as described in J. Inst. Brew, 1959, 65, 39–45, except that 1.5 g dried yeast was reconstituted in water at 38°C, made up to 250 ml with salts and water and 15 ml of this suspension taken for carrying out the test as described, had a 3 hour volume of 96 ml, 91% of which was retained after incubation for 7 days in nitrogen at 43°C. It had a Chorleywood bakery process proof time of 54 minutes and after incubation for 7 days in nitrogen at 43°C 84% of its original proof speed was retained. These values are all satisfactory.

EXAMPLE 2

Yeast cream of volume 1.5 litres containing 900 g of yeast cake (dry matter content about 33%) was treated with an aqueous suspension of 2.25 g Span 40 plus 2.25 g Span 60. The whole was mechanically stirred for 5 minutes and pressure filtered to give a friable cake. This was communited to obtain particles of 0.1 to 1.0 mm diameter, e.g. as in Example 1.

A portion (550 g) of the powder was loaded into a laboratory fluid-bed drier and dried for 104 minutes using air at a temperature of 55°C throughout the drying period. The yeast temperature reached 55°C after 74 minutes and remained at that value for a further 30 minutes.

The final moisture content was 35% by weight and the yeast had an activity such that the Fermentometer test gave a volume of 105 mls.

EXAMPLE 3

Example 2 was repeated except that 4.5 g Admul 57 was used instead of the Span mixture. The temperature rose to 55°C after 72 minutes and remained at that value for a further 30 minutes. The final moisture content was 3.3% and the Fermentometer volume was 97 mls.

I claim:

1. A method in which active dried yeast is made by drying particulate yeast in a fluidized bed that is fluidised using warm air and in which the yeast temperature is below 50°C until the dry matter content is above 80% by weight and is above 50°C. and no greater than 70°C. for at least the last 10 minutes of the drying.

2. A method according to claim 1 in which the temperature is above 50°C only when the dry matter content of the yeast is above 88% by weight.

3. A method according to claim 1 in which the yeast temperature is above 50°C. for 10 to 45 minutes at the end of drying.

4. A method according to claim 1 in which the entire fluidised bed drying process is conducted using a substantially constant rate of flow of air having a substantially constant moisture content and a substantially constant temperature range of from 50° to 60°C.

5. A method according to claim 1 in which the yeast particles subjected to the fluidised drying process are less than 1.7 mm in diameter and the active dried yeast is a powdered yeast.

6. A method according to claim 5 in which yeast particles have been made by comminuting moist yeast having a dry matter content of from 27 to 40% in a mill under high shear.

7. A method according to claim 5 in which the yeast particles have been made by spray drying liquid yeast to a dry matter content of from 40 to 50% by weight.

8. A method in which active dried yeast is made by forming yeast particles containing less than 50% by weight dry matter and which are less than 1.7 mm in diameter by comminution in a mill or by spray drying and then drying these particles to a dry matter content of at least 94% by weight in a fluidised bed using warm air, and in which the yeast temperature is below 50°C. until the dry matter content is above 80% by weight and is from above 50° and no greater than 60°C. for a period of 10 to 45 minutes at the end of the drying.

9. A method according to claim 8 in which the yeast includes a wetting agent.

10. A method according to claim 9 in which the wetting agent is an ester of a mixture of polyglycerols or of sorbitan and isosorbide with a $C_{16}$ to $C_{18}$ fatty acid or with a mixture of such acids and contains monoester, unesterified fatty acid and higher esters.

* * * * *